(12) United States Patent
Bhagalia et al.

(10) Patent No.: US 12,176,095 B2
(45) Date of Patent: Dec. 24, 2024

(54) MEDICAL SCANNER APPLICATION PLATFORM

(71) Applicant: GE Precision Healthcare LLC, Milwaukee, WI (US)

(72) Inventors: Roshni Bhagalia, Wales, WI (US); David Erik Chevalier, Menomonee Falls, WI (US); Fausto Espinal, Delafield, WI (US); Bradley J. Gabrielse, Brookfield, WI (US); Kenji Okabe, Pewaukee, WI (US); David Alexander Polyak, Marshall, WI (US); Nikhil Jones Tomy, New Berlin, WI (US); Khaleel Ahamad Nadaf, Bengaluru (IN)

(73) Assignee: GE Precision Healthcare LLC, Waukesha, WI (US)

( * ) Notice: Subject to any disclaimer, the term of this patent is extended or adjusted under 35 U.S.C. 154(b) by 314 days.

(21) Appl. No.: 17/532,482

(22) Filed: Nov. 22, 2021

(65) Prior Publication Data

US 2022/0172825 A1 Jun. 2, 2022

(30) Foreign Application Priority Data

Nov. 28, 2020 (IN) .............................. 202041051871

(51) Int. Cl.
*G06F 9/44* (2018.01)
*G06F 9/445* (2018.01)
(Continued)

(52) U.S. Cl.
CPC ............. *G16H 30/40* (2018.01); *G16H 40/67* (2018.01); *G16H 50/20* (2018.01); *H04L 63/0428* (2013.01)

(58) Field of Classification Search
CPC .... H04L 63/0428; H04L 67/125; H04L 67/34
See application file for complete search history.

(56) References Cited

U.S. PATENT DOCUMENTS

| 10,374,869 B2 * | 8/2019 | Jain ....................... H04L 41/046 |
| 2015/0149506 A1 * | 5/2015 | Raizada ................ G06F 16/289 |
| | | 707/792 |

(Continued)

FOREIGN PATENT DOCUMENTS

| CN | 102598049 A  * | 7/2012 | ........... G06F 19/321 |
| EP | 3249565 A2 * | 11/2017 | ............. G16H 30/20 |
| JP | 2020500378 A  * | 1/2020 | |

OTHER PUBLICATIONS

William J. Allen, Platform for Automated Real-Time High Performance Analytics on Medical Image Data, 2018, pp. 318-324. https://ieeexplore.ieee.org/stamp/stamp.jsp?arnumber=8100868 (Year: 2018).*

(Continued)

*Primary Examiner* — Mongbao Nguyen
(74) *Attorney, Agent, or Firm* — Amin, Turocy & Watson, LLP

(57) ABSTRACT

Medical scanner application platforms and associated components (e.g., using a computerized tool) is enabled. For example, a system, can comprise: a processor, and a memory that stores executable instructions that, when executed by the processor, facilitate performance of operations, comprising: determining, based on package schema data representative of a package schema of an application received via a network, one or more attributes of the application, based on the one or more attributes of the application, determining one or more constraints of the application applicable to a medical scanner communicatively coupled to the system via (Continued)

an agent of the medical scanner, and storing the application in an application database accessible to the agent of the medical scanner.

20 Claims, 13 Drawing Sheets

(51) Int. Cl.
*G06F 9/455* (2018.01)
*G16H 30/40* (2018.01)
*G16H 40/67* (2018.01)
*G16H 50/20* (2018.01)
*H04L 9/40* (2022.01)

(56) References Cited

U.S. PATENT DOCUMENTS

| | | | | |
|---|---|---|---|---|
| 2015/0180951 | A1* | 6/2015 | Barnreuther | G06F 9/4451 709/201 |
| 2018/0330317 | A1* | 11/2018 | Sepulveda | G06F 16/23 |
| 2020/0168335 | A1* | 5/2020 | Lassoued | G16H 40/67 |
| 2020/0402674 | A1* | 12/2020 | DeBates | G16H 40/67 |
| 2021/0233664 | A1* | 7/2021 | Colley | G16H 50/70 |

OTHER PUBLICATIONS

S. Pillai Thara, A Generic Layer Based Approach for Design of Software for Medical Imaging Systems, 2018, pp. 1-5. https://ieeexplore.ieee.org/stamp/stamp.jsp?tp=&arnumber=8748715 (Year: 2018).*

English translation, Okuyama et al. (CN 102598049 A), 2012, pp. 1-23. (Year: 2012).*

English translation, Dominick et al. (EP 3249565 A2), 2017, pp. 1-14. (Year: 2014).*

* cited by examiner

MEDICAL SCANNER APPLICATION PLATFORM

CROSS-REFERENCE TO RELATED APPLICATIONS

This application claims priority to India Provisional Application No. 202041051871, filed Nov. 28, 2020, entitled "SYSTEMS, APPARATUSES, AND METHODS FOR SCANNER APPLICATION SERVICES." The entirety of the aforementioned application is hereby incorporated herein by reference.

TECHNICAL FIELD

The disclosed subject matter relates to medical scanners and, more particularly, to medical scanner platforms that enable improved integration between medical devices and associated services or applications.

BACKGROUND

Digital Imaging and Communications in Medicine (DICOM) is a standard for communication/management of medical imaging information and related data. Unless an interface between an application and a scanner uses DICOM, integrating an application with certain platforms can require additional software development and installation of updates on a scanner console. Modifications to a scanner console is both time consuming and expensive due to verification and validation requirements associated with medical devices. In this regard, each time an application is added to a scanner, the scanner must be updated to trigger or execute that application. This can lead to scanner downtime and reduced availability, and thus increased costs and diminished patient outcomes.

The above-described background relating to medical scanner platforms is merely intended to provide a contextual overview of some current issues and is not intended to be exhaustive. Other contextual information may become further apparent upon review of the following detailed description.

DETAILED DESCRIPTION

Figure 1:
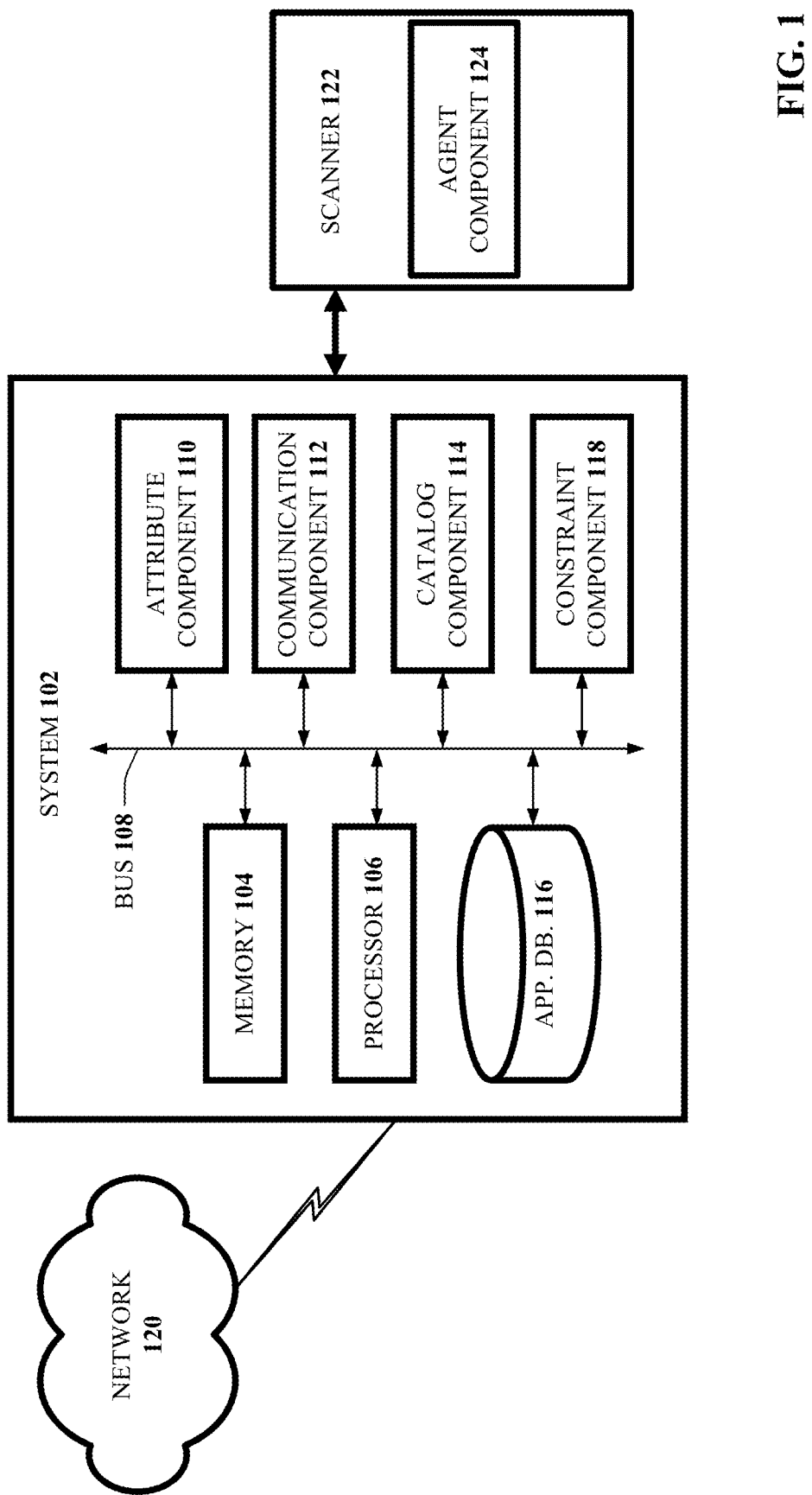
FIG. 1 is a block diagram of an exemplary system in accordance with one or more embodiments described herein.

The subject disclosure is now described with reference to the drawings, wherein like reference numerals are used to refer to like elements throughout. In the following description, for purposes of explanation, numerous specific details are set forth in order to provide a thorough understanding of the subject disclosure. It may be evident, however, that the subject disclosure may be practiced without these specific details. In other instances, well-known structures and devices are shown in block diagram form in order to facilitate describing the subject disclosure.

As alluded to above, medical scanners and associated components and platforms can be improved in various ways, and various embodiments are described herein to this end and/or other ends.

The following disclosed subject matter enables an architecture which can remain common on among various scanner deployment scenarios and size scales. The architecture can support a variety of deployment models while maintaining platform security. Architectures and corresponding systems and processes herein can utilize decoupled layers and/or defined interfaces at layer integration points. Industry standards can be maintained with commercial support for critical technologies with minimal or even zero vendor lock-in. System resources can be optimized while meeting application performance requirements. Architectures and corresponding systems and processes herein can support high-availability system configurations, without a need for specialized accommodations.

Embodiments herein can enable new functionality to be added to medical scanners (e.g., via new application installations) without invalidating a verified and validated configuration of a medical scanner because, for instance, various embodiments herein comprise platforms on which new applications can be added without modification to an associated medical scanner. In this regard, applications themselves can be verified and/or validated, and added asynchronously to a lifecycle of a medical scanner herein. Such a medical scanner can thus become an improved piece of equipment without needing to make additional hardware updates at the medical scanner. Such improvements can be made without disrupting use of the medical scanners.

According to an embodiment, a system can comprise a memory that stores computer executable components, and a processor that executes the computer executable components stored in the memory, wherein the computer executable components comprise: an attribute component that determines, based on package schema data representative of a package schema of an application received via a network, one or more attributes of the application, a constraint component that, based on the one or more attributes of the application, determines one or more constraints of the application applicable to a medical scanner communicatively coupled to the system via an agent of the medical scanner, and a catalog component that stores the application in an application database accessible to the agent of the medical scanner.

In various embodiments, the computer executable components can further comprise: a communication component that receives, from the agent of the medical scanner, a request to execute the application, and an execution component that, in response to the communication component receiving the request to execute the application, executes the application, wherein the application and the one or more constraints are accessible via a graphical user interface of the medical scanner. In some implementations, the communication component can receive imaging data representative of a medical scan captured via the medical scanner, and wherein the execution component executes the application to process the imaging data. In further embodiments, in response to the imaging data being processed using the application, the communication component can send the imaging data to the medical scanner and/or to a device communicatively coupled to the system via the network.

In some embodiments, the application can comprise a remote application of a group of remote applications stored in the application database, the catalog component can generate a catalog of applications executable via the medical scanner, and the catalog of applications can comprise the group of remote applications and local applications stored in a memory of the medical scanner. In further embodiments, the request to execute the application can be received in response to a determination by the catalog component that the application comprises the remote application.

In an implementation, the computer executable components can further comprise a machine learning component that determines the package schema based on machine learning applied to past package schemas of past applications other than the application. In further implementations, the machine learning component can determine the one or more constraints based on the machine learning applied to past constraints of the past applications other than the application.

In some embodiments, the application can comprise a patient setup workflow application. In further embodiments, the application can comprise a remote reconstruction application. In additional embodiments, the application can comprise a post-processing application.

In another embodiment, a non-transitory machine-readable medium can comprise executable instructions that, when executed by a processor, facilitate performance of operations, comprising: determining available applications from a catalog of applications executable via a medical scanner, wherein the catalog of applications comprises local applications stored in a memory of the medical scanner and remote applications stored on a server communicatively coupled to the medical scanner, in response to receiving, via a graphical user interface of the medical scanner, a request to execute an application of the available applications, determining whether the application comprises a local application of the local applications or a remote application of the remote applications, and in response to a determination that the application comprises the remote application, executing the application via the server.

In various embodiments, executing the application via the server can comprise: initiating the application via the server, sending, to the application, scan data representative of a medical scan obtained via the medical scanner, in response to the scan data being processed via the application resulting in processed medical image data, receiving the processed medical image data from the application, and rendering, via the graphical user interface, a medical image based on the processed medical image data. In further embodiments, executing the application via the server can comprise: initiating the application via the server, sending, to the server, patient workflow data obtained via the graphical user interface of the medical scanner, and in response to the patient workflow data being processed via the application, initiating a medical scan via the medical scanner.

In some embodiments, communication between the server and the medical scanner can be encrypted.

According to yet another embodiment, a method can comprise: determining, by a device comprising a processor and based on package schema data representative of a package schema of an application received via a network, one or more attributes of the application, based on the one or more attributes of the application, determining, by the device, one or more constraints of the application applicable to a medical scanner communicatively coupled to the device via an agent of the medical scanner, and storing, by the device, the application in an application database accessible to the agent of the medical scanner.

In various embodiments, the one or more constraints can comprise one or more features of the medical scanner required by the application.

In various implementations, the medical scanner can comprise a computed tomography scanner, a positron emission tomography scanner, magnetic resonance imaging scanner, or an ultrasound scanner.

In some embodiments, the medical scanner can be located in a first location comprising a medical facility, and the device can be located in a second location, different from the first location.

It should be appreciated that additional manifestations, configurations, implementations, protocols, etc. can be utilized in connection with the following components described herein or different/additional components as would be appreciated by one skilled in the art.

Turning now to FIG. 1, there is illustrated an example, non-limiting system 102 in accordance with one or more embodiments herein. System 102 can comprise a computerized tool, which can be configured to perform various operations relating to medical scanner application platforms and associated components. The system 102 can comprise one or more of a variety of components, such as memory 104, processor 106, bus 108, attribute component 110, communication component 112, catalog component 114, application database 116, and/or constraint component 118. The system 102 can be communicatively coupled to a medical scanner 122 (e.g., via a network 120).

In various embodiments, one or more of the memory 104, processor 106, bus 108, attribute component 110, communication component 112, catalog component 114, application database 116, constraint component 118, and/or medical scanner 122 can be communicatively or operably coupled (e.g., over a bus or wireless network) (e.g., network 120) to one another to perform one or more functions of the system 102.

Seamless integration between applications on an edge device (e.g., a system 102, system 202, system 302, server 416, system 520, or another suitable system) and a medical scanner (e.g., a medical scanner 122, system 402, system 502, or another suitable medical equipment) is enabled. An agent (e.g., agent component 124) can be installed on a medical equipment (e.g., a medical scanner 122) which can comprise a service that can host profiles of applications stored on the edge device. The agent can further enable one or more applications located in the edge device to automatically integrate with the medical scanner, without requiring additional software updates to the medical scanner itself.

According to an embodiment, the attribute component 110 can determine, based on package schema data representative of a package schema of an application received via a network (e.g., received via a communication component 112), one or more attributes of the application. In various embodiments, package schema herein can define a profile of an application (e.g., profile information) and/or can include attributes such as application version information, application type, URL, or other suitable attributes, which can be copied into the catalog component 114. Additionally, or alternatively, such attributes can comprise application type (e.g., postprocessing application, reconstruction application, or another suitable application) and associated specifications and/or metadata. It is noted that the communication component 112 can comprise the hardware required to implement a variety of communication protocols (e.g., infrared ("IR"), shortwave transmission, near-field communication ("NFC"), Bluetooth, Wi-Fi, long-term evolution ("LTE"), 3G, 4G, 5G, 6G, global system for mobile communications ("GSM"), code-division multiple access ("CDMA"), satellite, visual cues, radio waves, etc.)

According to an embodiment, the constraint component 118 can, based on the one or more attributes of the application, determine one or more constraints of the application applicable to a medical scanner (e.g., medical scanner 122) communicatively coupled to the system via an agent (e.g., agent component 124) of the medical scanner 122. In various embodiments, constraints herein can comprise or be associated with one or more features of a medical scanner (e.g., and/or as required by an application herein). In this regard, such constraints can comprise features enabled or disabled on a medical scanner (e.g., medical scanner 122) and/or information conveyable to the medical scanner 122. It is noted that medical scanners herein can comprise one or more of a computed tomography (CT) scanner, X-Ray scanner, magnetic resonance imaging (MRI) scanner, positron emission tomography (PET) Scanner, ultrasound, or another suitable medical imaging scanner.

According to an embodiment, the catalog component 114 can store the application in an application database (e.g., application database 116) accessible to the agent (e.g., agent component 124) of the medical scanner 122. In various embodiments, the agent component 124 can facilitate integration with any component compatible with the agent component 124. In this regard, upon installation of an agent component 124 on a medical scanner 122, integration/installation of new applications does not require any physical changes or updates at the medical scanner 122, thus decreasing downtime while increasing efficiency and patient outcomes. It can be appreciated that the agent component 124 can be operable on virtually any medical scanner, thus enabling integration with legacy scanners or new scanners of virtually any brand. The foregoing can facilitate seamless triggering of applications (e.g., past, present, or future applications) without needing to update a medical scanner 122 for each application.

According to an embodiment, the agent component 124 can identify various features, constraints, or limitations of an associated medical scanner 122. It is noted the catalog component 114 can further store various profiles, schemas, and/or applications associated with the system 102. In further embodiments, the catalog component 114 can facilitate licensing or check a license corresponding to an application (e.g., via an application constraints proxy). This can enable/disable various applications (e.g., on a medical scanner 122).

In various implementations, applications herein can comprise one or more of a variety of applications associated with a medical scanner or associated systems or components. For example, an application herein can comprise one or more of a patient setup workflow application, a remote reconstruction application, a post-processing application, thin clients (e.g., a web browser), thick clients (e.g., an application requiring an installation), or other suitable applications as would be understood by one skilled in the art. It is noted that applications herein can comprise a standalone user interface or can utilize a defined uniform user interface framework.

According to an embodiment, a system 102 herein and a medical scanner 122 can be located in one or more of variety of locations. For instance, the system 102 and medical scanner 122 can both be located "on-prem" or within the same medical facility. In other embodiments, the system 102 and medical scanner 122 can be located in different locations. For example, the medical scanner 122 can be located in a first location (e.g., comprising a medical facility), and the system 102 can be located in a second location, different from the first location (e.g., not the medical facility). In this regard, the system 102 can comprise a cloud-based system 102 or can be otherwise externally located and communicatively coupled to a medical scanner 122. For instance, the system 102 can be located in a first medical facility, and the medical scanner 122 can be located in a second medical facility, separate from the first medical facility.

Figure 2:
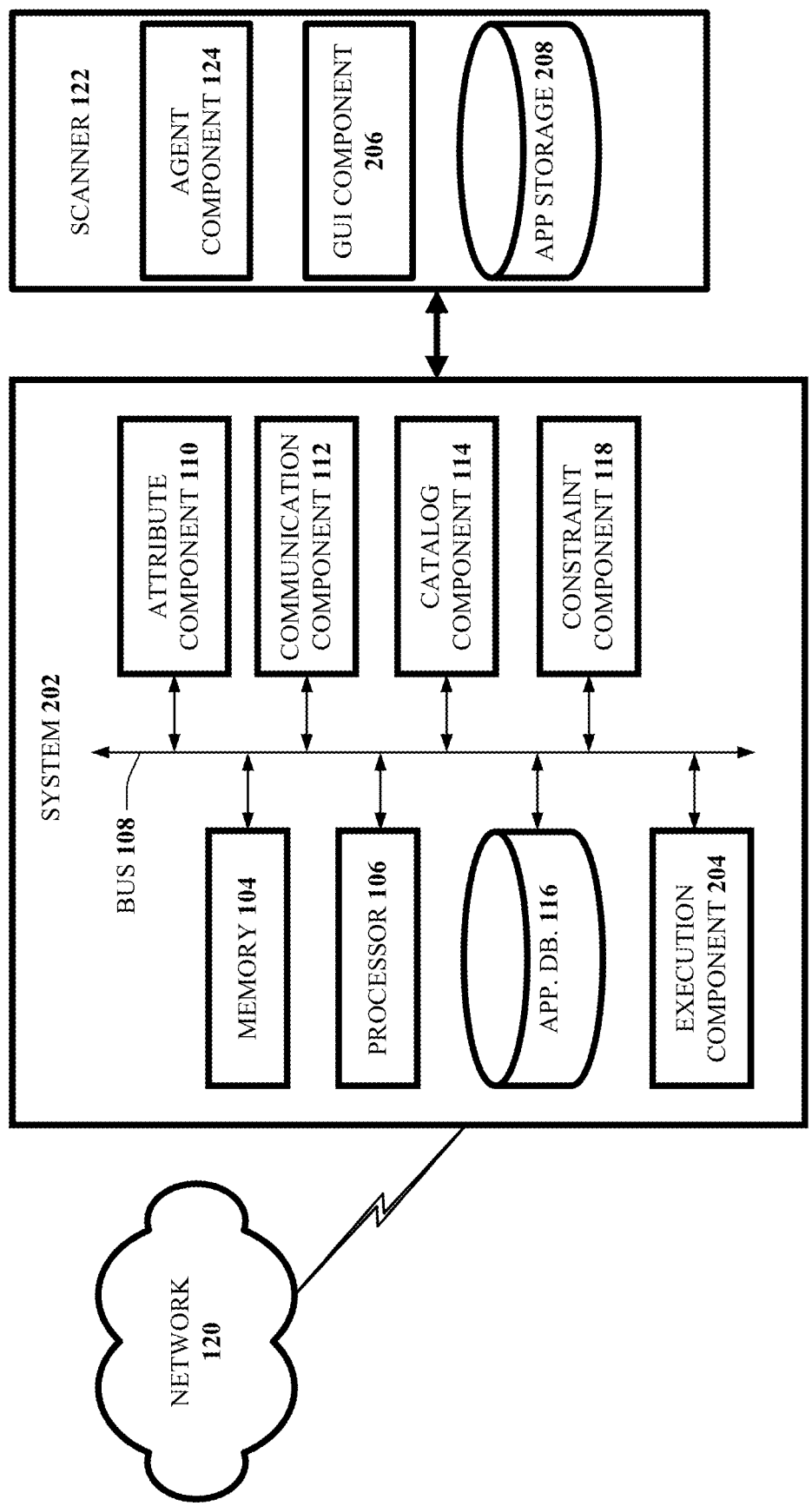
FIG. 2 is a block diagram of an exemplary system in accordance with one or more embodiments described herein.

Turning now to FIG. 2, there is illustrated an example, non-limiting system 202 in accordance with one or more embodiments herein. System 202 can comprise a computerized tool, which can be configured to perform various operations relating to medical scanner application platforms and associated components. The system 202 can be similar to system 102, and can comprise one or more of a variety of components, such as memory 104, processor 106, bus 108, attribute component 110, communication component 112, catalog component 114, application database 116, and/or constraint component 118. The system 202 can be communicatively coupled to a medical scanner 122 (e.g., via a network 120). The system 202 can additionally comprise an execution component 204. It is further noted that the medical scanner 122 can comprise a graphical user interface (GUI) component 206 and/or local application storage 208.

In various embodiments, one or more of the memory 104, processor 106, bus 108, attribute component 110, communication component 112, catalog component 114, application database 116, constraint component 118, execution component 204, and/or medical scanner 122 can be communicatively or operably coupled (e.g., over a bus or wireless network) (e.g., network 120) to one another to perform one or more functions of the system 202.

According to an embodiment, the communication component 112 can receive, from the agent component 124 of the medical scanner (e.g., medical scanner 122), a request to execute an application. In this regard, the execution component 204 can execute the application. It is noted that the application and the one or more constraints can be accessible via a GUI component 206 of the medical scanner 122. In one or more embodiments, the GUI component 206 can comprise a touch screen or can comprise a screen and an input device (e.g., a keyboard, mouse, or another suitable input device).

According to an embodiment, the communication component 112 can receive imaging data representative of a medical scan captured via the medical scanner 122. In this regard, the execution component 204 can process the imaging data using the application. In additional embodiments, the communication component 112 can, in response to processing (e.g., via the execution component 204) the imaging data using the application, send the imaging data to the medical scanner 122. In further embodiments, the communication component 112 can, in response to processing (e.g., via the execution component 204) the imaging data using the application, send the imaging data to a device communicatively coupled to the system via the network (e.g., the network 120).

In various implementations, the application can comprise a remote application (e.g., not stored in an application storage 208) of a group of remote applications stored in the application database (e.g., application database 116). In this regard, the catalog component 114 can generate and/or update a catalog of applications executable via the medical scanner 122. Further in this regard, the catalog of applications can comprise the group of remote applications (e.g., stored in the application database 116) and local applications stored in a memory (e.g., application storage 208) of the medical scanner 122. According to an embodiment, a request to execute an application herein (e.g., via the execution component 204) can be received (e.g., via the communication component 112) in response to a determination (e.g., by the catalog component 114 and/or the agent component 124 of the medical scanner 122) that the application comprises a remote application.

Figure 3:
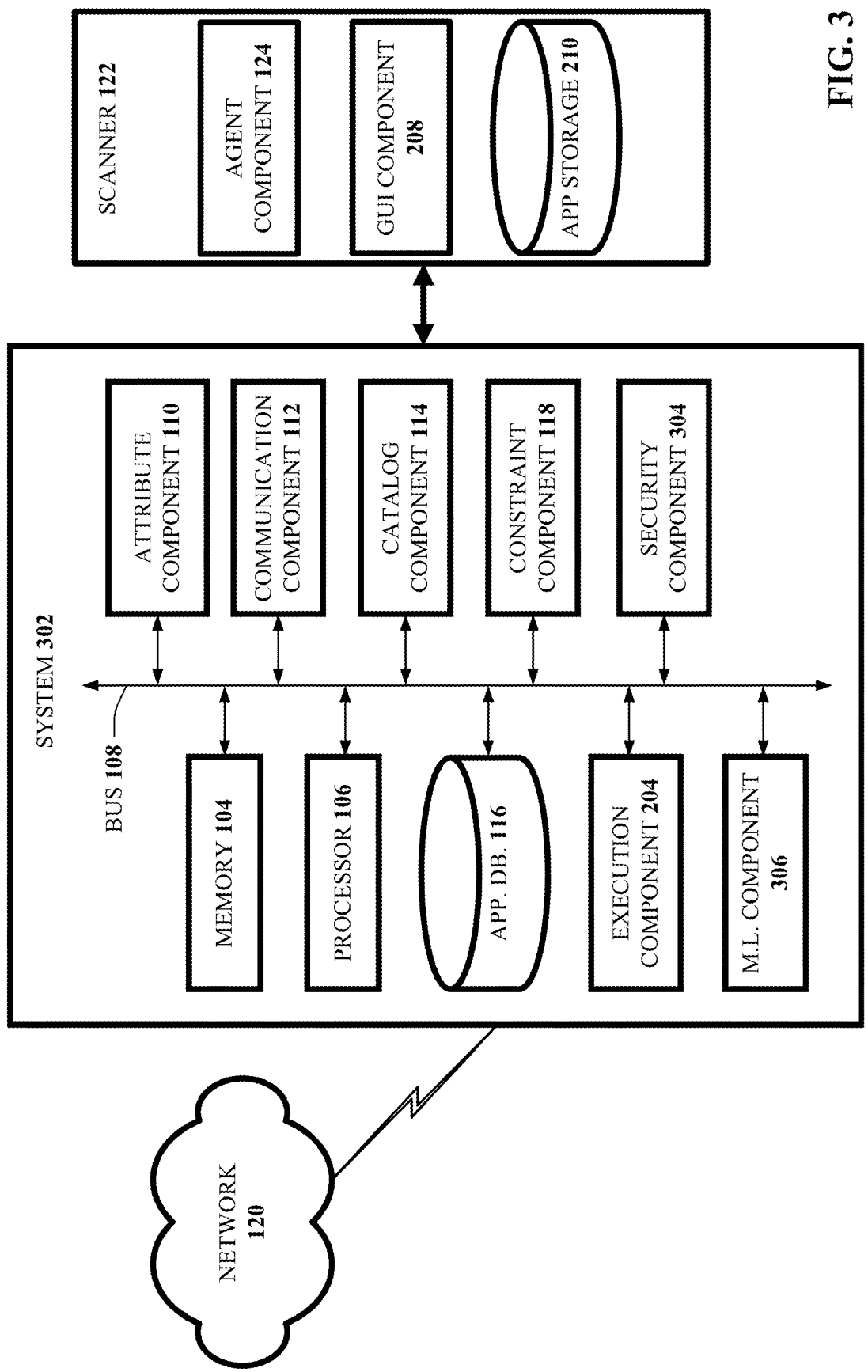
FIG. 3 is a block diagram of an exemplary system in accordance with one or more embodiments described herein.

Turning now to FIG. 3, there is illustrated an example, non-limiting system 302 in accordance with one or more embodiments herein. System 302 can comprise a computerized tool, which can be configured to perform various operations relating to medical scanner application platforms and associated components. The system 302 can be similar to system 202, and can comprise one or more of a variety of components, such as memory 104, processor 106, bus 108, attribute component 110, communication component 112, catalog component 114, application database 116, constraint component 118, and/or execution component 204. The system 302 can be communicatively coupled to a medical scanner 122 (e.g., via a network 120). The system 302 can additionally comprise a security component 304 and/or machine learning (M.L.) component 306.

In various embodiments, one or more of the memory 104, processor 106, bus 108, attribute component 110, communication component 112, catalog component 114, application database 116, constraint component 118, execution component 204, security component 304, M.L. component 306, and/or medical scanner 122 can be communicatively or operably coupled (e.g., over a bus or wireless network) (e.g., network 120) to one another to perform one or more functions of the system 302.

According to an embodiment, package schema herein can be determined based on machine learning applied (e.g., by the M.L. component 306) to past package schemas of past applications (e.g., other than an instant application). In this regard, the M.L. component 306 generate a package schema model using the machine learning applied to the past package schemas of past applications (e.g., other than in instant application herein). The M.L. component 306 can thus utilize the package schema model to analyze an application in order to determine package schema (e.g., rather than receiving the package schema along with the application). In further embodiments, constrains herein can be determined based on machine learning applied (e.g., by the M.L. component 306) to past constraints of past applications herein. In this regard, the M.L. component 306 generate a constrains model using the machine learning applied to the past constraints of past applications (e.g., other than in instant application herein). The M.L. component 306 can thus utilize the constrains model to analyze an application in order to determine the constrains.

According to an embodiment, the security component 304 can facilitate an encrypted communication (e.g., via the communication component 112) with the medical scanner 122. In this regard, communications of medical data herein between the system 302 and medical scanner 122 can be protected against unauthorized viewing.

Various embodiments herein can employ artificial-intelligence or machine learning systems and techniques to facilitate learning user behavior, context-based scenarios, preferences, etc. in order to facilitate taking automated action with high degrees of confidence. Utility-based analysis can be utilized to factor benefit of taking an action against cost of taking an incorrect action. Probabilistic or statistical-based analyses can be employed in connection with the foregoing and/or the following.

It is noted that systems and/or associated controllers, servers, or machine learning components herein can comprise artificial intelligence component(s) which can employ an artificial intelligence (A.I.) model and/or M.L. or an M.L. model that can learn to perform the above or below described functions (e.g., via training using historical training data and/or feedback data).

In some embodiments, M.L. component 306 can comprise an A.I. and/or M.L. model that can be trained (e.g., via supervised and/or unsupervised techniques) to perform the above or below-described functions using historical training data comprising various context conditions that correspond to various augmented network optimization operations. In this example, such an A.I. and/or M.L. model can further learn (e.g., via supervised and/or unsupervised techniques) to perform the above or below-described functions using training data comprising feedback data, where such feedback data can be collected and/or stored (e.g., in memory) by the M.L. component 306. In this example, such feedback data can comprise the various instructions described above/below that can be input, for instance, to a system herein, over time in response to observed/stored context-based information.

A.I./M.L. components herein can initiate an operation(s) associated with a based on a defined level of confidence determined using information (e.g., feedback data). For example, based on learning to perform such functions described above using feedback data, performance information, and/or past performance information herein, an M.L. component 306 herein can initiate an operation associated with determining various thresholds herein.

In an embodiment, the M.L. component 306 can perform a utility-based analysis that factors cost of initiating the above-described operations versus benefit. In this embodiment, the M.L. component 306 can use one or more additional context conditions to determine various thresholds herein.

To facilitate the above-described functions, a M.L. component 306 herein can perform classifications, correlations, inferences, and/or expressions associated with principles of artificial intelligence. For instance, the M.L. component 306 can employ an automatic classification system and/or an automatic classification. In one example, the M.L. component 306 can employ a probabilistic and/or statistical-based analysis (e.g., factoring into the analysis utilities and costs) to learn and/or generate inferences. The M.L. component 306 can employ any suitable machine-learning based techniques, statistical-based techniques and/or probabilistic-based techniques. For example, the M.L. component 306 can employ expert systems, fuzzy logic, support vector machines (SVMs), Hidden Markov Models (HMMs), greedy search algorithms, rule-based systems, Bayesian models (e.g., Bayesian networks), neural networks, other non-linear training techniques, data fusion, utility-based analytical systems, systems employing Bayesian models, and/or the like. In another example, the M.L. component 306 can perform a set of machine-learning computations. For instance, the M.L. component 306 can perform a set of clustering machine learning computations, a set of logistic regression machine learning computations, a set of decision tree machine learning computations, a set of random forest machine learning computations, a set of regression tree machine learning computations, a set of least square machine learning computations, a set of instance-based machine learning computations, a set of regression machine learning computations, a set of support vector regression machine learning computations, a set of k-means machine learning computations, a set of spectral clustering machine learning computations, a set of rule learning machine learning computations, a set of Bayesian machine learning computations, a set of deep Boltzmann machine computations, a set of deep belief network computations, and/or a set of different machine learning computations.

Figure 4:
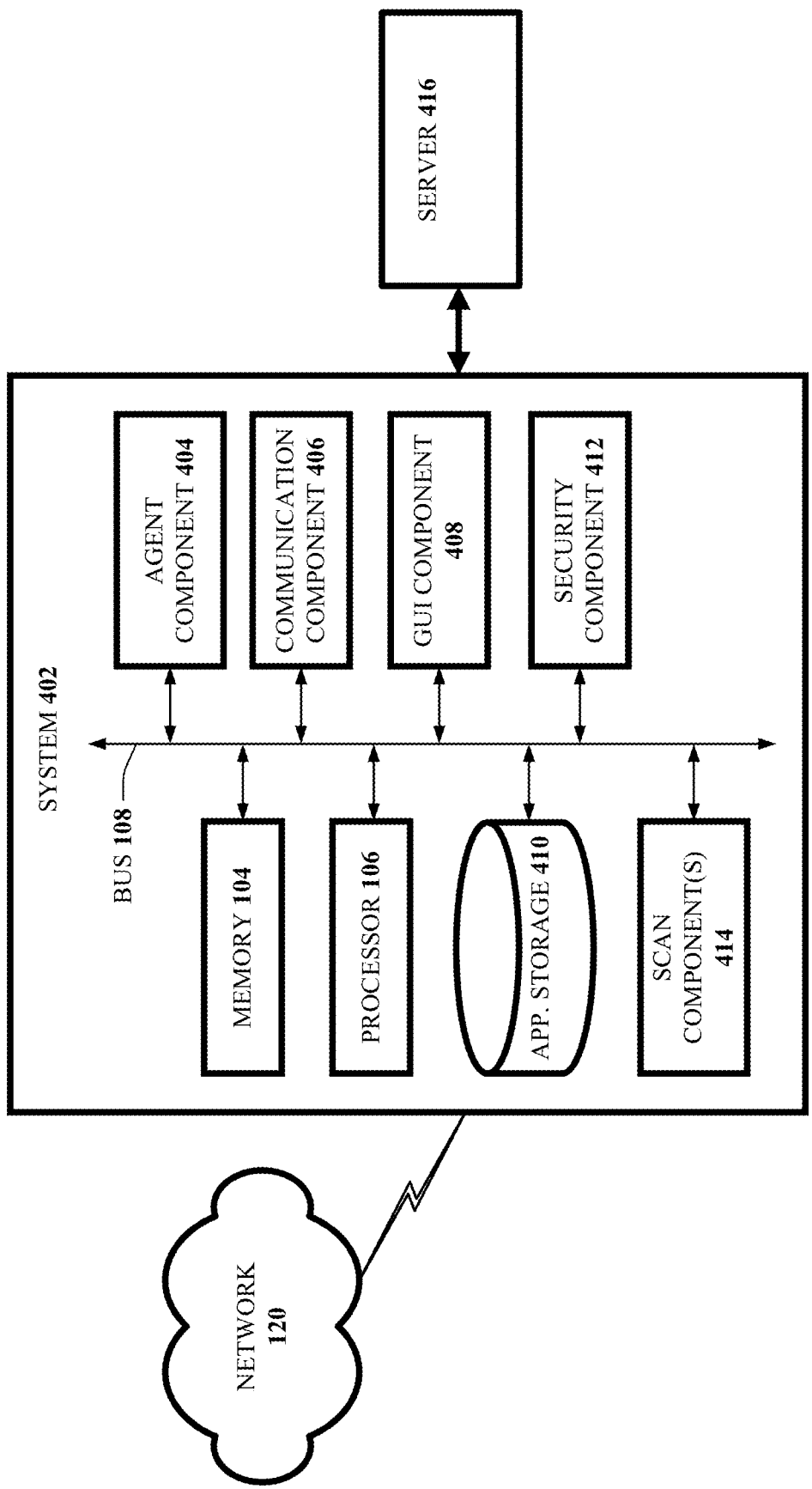
FIG. 4 is a block diagram of an exemplary system in accordance with one or more embodiments described herein.

Turning now to FIG. 4, there is illustrated an example, non-limiting system 402 in accordance with one or more embodiments herein. System 402 can comprise a computerized tool, which can be configured to perform various operations relating to medical scanner application platforms and associated components. The system 402 can comprise one or more of a variety of components, such as memory 104, processor 106, bus 108, agent component 404, communication component 406, GUI component 408, application storage 410, security component 412, and/or scan component 414. The system 402 can be communicatively coupled to a server 416 (e.g., via a network 120). In some implementations, the server 416 can comprise one or more of the system 102, system 202, and/or system 302.

In various embodiments, one or more of the memory 104, processor 106, bus 108, agent component 404, communication component 406, GUI component 408, application storage 410, security component 412, scan component 414, and/or server 416 can be communicatively or operably coupled (e.g., over a bus or wireless network) (e.g., network 120) to one another to perform one or more functions of the system 402.

It is noted that the agent component 404 can be similar to the agent component 124. According to an embodiment, the agent component 404 can determine available applications from a catalog of applications executable via a medical scanner (e.g., a medical scanner comprising a system 402). In this regard, such a catalog of applications can comprise local applications stored in a memory of the medical scanner (e.g., in application storage 410) and remote applications stored on a server (e.g., server 416) communicatively coupled (e.g., via the communication component 406) to the medical scanner (e.g., medical scanner 122). It is further noted the communication component 406 can be similar to the communication component 112.

According to an embodiment, the GUI component 408 can be similar to the GUI component 206, and can receive various inputs and/or requests to execute an application (e.g., of available applications). In this regard, the agent component 404 can determine whether a request to execute an application is associated with a remote application (e.g., stored on the server 416) and/or a local application (e.g., stored in the application storage 410). Further in this regard, the agent component 404 can execute a remote application via the server 416 (e.g., in response to a determination by the agent component 404 that an application comprises a remote application).

In various embodiments, executing an application via a server herein (e.g., server 416) can comprise initiating (e.g., using the agent component 404) the application via the server (e.g., server 416), sending (e.g., using the communication component 406), to the application, scan data representative of a medical scan obtained via the medical scanner (e.g., using a scan component 414), receiving the processed medical image data from the application resulting in processed medical image data (e.g., in response to the scan data being processed via the application), and rendering (e.g., via the GUI component 408), a medical image based on the processed medical image data. In further embodiments, executing an application via server herein (e.g., server 416) can comprise initiating the application via the server (e.g., server 416), sending (e.g., using the communication component 406), to the server, patient workflow data obtained via the GUI component 408, and initiating (e.g., using the agent component 404) a medical scan via the medical scanner (e.g., using one or more of the scan component 414) (e.g., in response to the patient workflow data being processed via the application).

According to an embodiment, the security component 412 can facilitate an encrypted communication (e.g., via the communication component 406) with the server 416. In this regard, communications of medical data herein between the system 402 and server 416 can be protected against unauthorized viewing.

Figure 5:
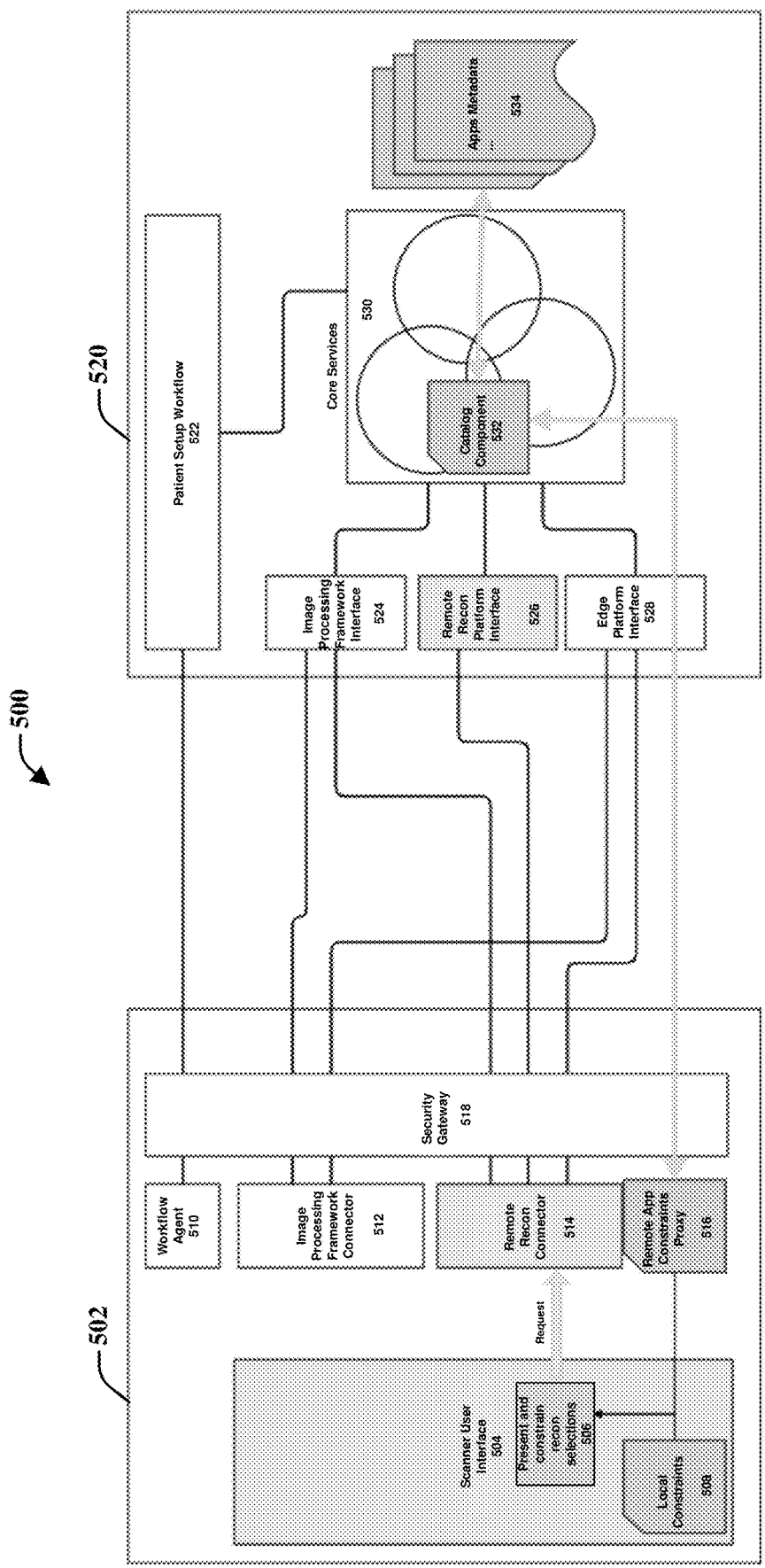
FIG. 5 is a block diagram of an exemplary system topology in accordance with one or more embodiments described herein.

FIG. 5 illustrates a block diagram of an exemplary system topology 500 in accordance with one or more embodiments described herein. In various embodiments, system 502 can comprise a medical scanner herein (e.g., medical scanner 122 and/or system 402), and system 520 can comprise an edge system herein (e.g., system 102, system, 202, system 302, and/or server 416).

According to an embodiment, system 502 can comprise a user interface (UI) 504 (e.g., a GUI described herein). In various embodiments, the UI 504 can be employable to invoke an application herein. In further embodiments, the UI 504 can, at 506, present and/or constrain reconstruction selections (e.g., via a GUI). The UI 504 can additionally comprise local constraints 508. In various implementations, local constraints 508 can be based on hardware and/or software limitations of the system 502. For instance, system 502 hardware may only be capable of presenting or operating with certain reconstruction selections. Additionally, or alternatively, the system 502 may be licensed to operate only with certain defined reconstruction selections. According to an embodiment, the remote application constraints proxy 516 can communicate the local constraints 508 to the system 520 (e.g., to a catalog component 532) in order to ensure that only valid combinations of applications and/or selections are selectable via the scanner user interface 504. In this regard, once a user inputs a selection via the UI 504, the inputs from reconstruction selections 506 can be provided to the remote reconstruction connector at 514, which can communicate the selection (e.g., through the security gateway 518) to the remote reconstruction platform interface 526, which can then invoke the application through the catalog component 532.

It is noted that the system 502 can comprise workflow agent 510, an image processing framework connector 512, a remote reconstruction connector 514, a remote application constraints proxy 516, and/or a security gateway 518. According to an embodiment, the security gateway 518 can comprise a bootstrap or provide HTTPS security (e.g., encryption) for communication between the system 502 and system 520. In an embodiment, the workflow agent 510 can be communicatively coupled to patient setup workflow 522 of the system 520. The image processing framework connector 512 can be communicatively coupled to the image processing framework interface 524 and the remote reconstruction platform interface 526. The remote reconstruction connector 514 can be communicatively coupled to the image processing framework interface 524, the remote reconstruction platform interface 526, and the edge platform interface 528. The remote application constraints proxy 516 can be communicatively coupled to the catalog component 532, which can be communicatively coupled to the applications metadata 534. In this regard, applications metadata 534 can be provided to the catalog component 532. It can be appreciated that core services 530 can comprise the catalog component 532.

The catalog component 532 can store a plurality of applications, read associated application metadata, and/or communicate with the remote application constraints proxy 516. The system 502, using the remote application constraints proxy 516, can determine which settings are valid depending on, for instance, a scan mode of the system 502 or settings of the system 502. In this regard, a user of the system 502 can be prevented from making an invalid application selection on the UI 504. Therefore, according to an example, when a scan is conducted using a system 502, only available applications, options, or services are presented to the via the UI 504. The foregoing can enable a system 502 to communicate over a common framework with any of the applications supported by the system 520, while the remote application constraints proxy 516 can prevent use of any applications that are not operable (e.g., hardware constraints or software constraints noted as indicated in local constraints 508).

Figure 6:
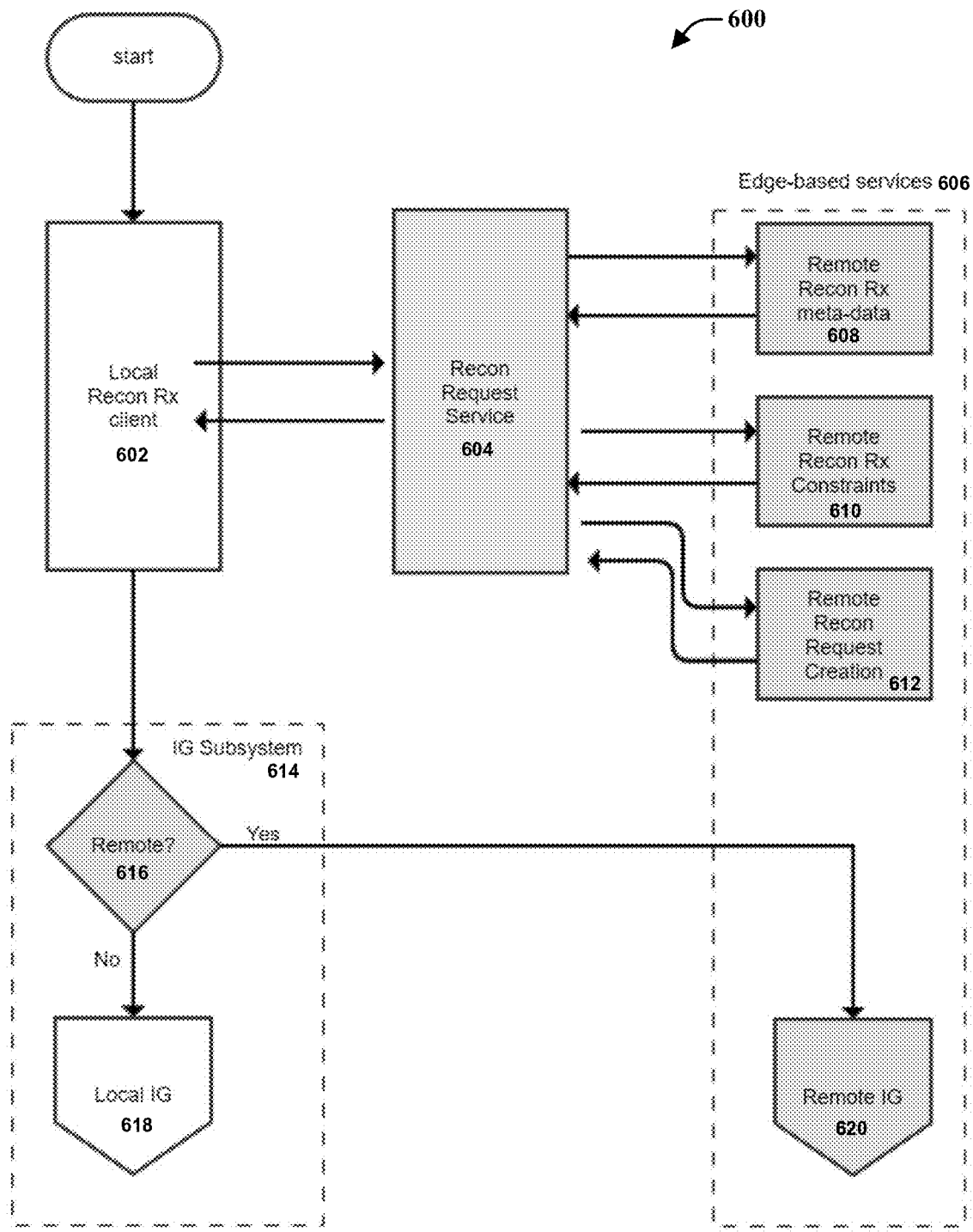
FIG. 6 is a block diagram of an exemplary system topology in accordance with one or more embodiments described herein.

With reference to FIG. 6, there is illustrated a system topology 600 in accordance with various embodiments described herein. The system topology 600 illustrates both local reconstruction and remote reconstruction. In this regard, system topology 600 can be representative of processes that occur between present and constrain reconstructions 506 and remote reconstruction connector 514, in addition to processes that occur between remote reconstruction connector 514 and remote reconstruction platform interface 526 after a user creates reconstruction request via a scanner UI 504. In this regard, the following can ensure that a valid message representative of a reconstruction request can be sent to a local application that facilitates image reconstruction or a remote application. A local reconstruction prescription client 602 can be communicatively coupled to a reconstruction request service 604 and an image generation (IG) subsystem 614 (e.g., a reconstruction subsystem) of the local reconstruction prescription client 602. For remote reconstruction, the reconstruction request service 604 can be communicatively coupled with edge-based services 606 in order to determine remote reconstruction prescription metadata 608 (e.g., of an application), remote reconstruction prescription constraints 610 (e.g., valid combinations), and remote reconstruction request creation 612 (e.g., how to make an associated request). The reconstruction request service 604 can retrieve the remote reconstruction prescription metadata 608, the remote reconstruction prescription constraints 610, and/or the remote reconstruction request creation 612, and pass the foregoing information back to the local reconstruction prescription client 602. At 616, if remote reconstruction is to be conducted, remote image generation is conducted at 620 of the edge-based services 606. If, at 616, remote reconstruction is not to be conducted, local image generation occurs at 618 of the image generation subsystem 614. It is noted that image reconstruction requests can be flagged as local or remote, and local resources of the local reconstruction prescription client 602 can track a job status. The foregoing can enable seamless reconstruction, whether conducted remotely or locally.

Figure 7:
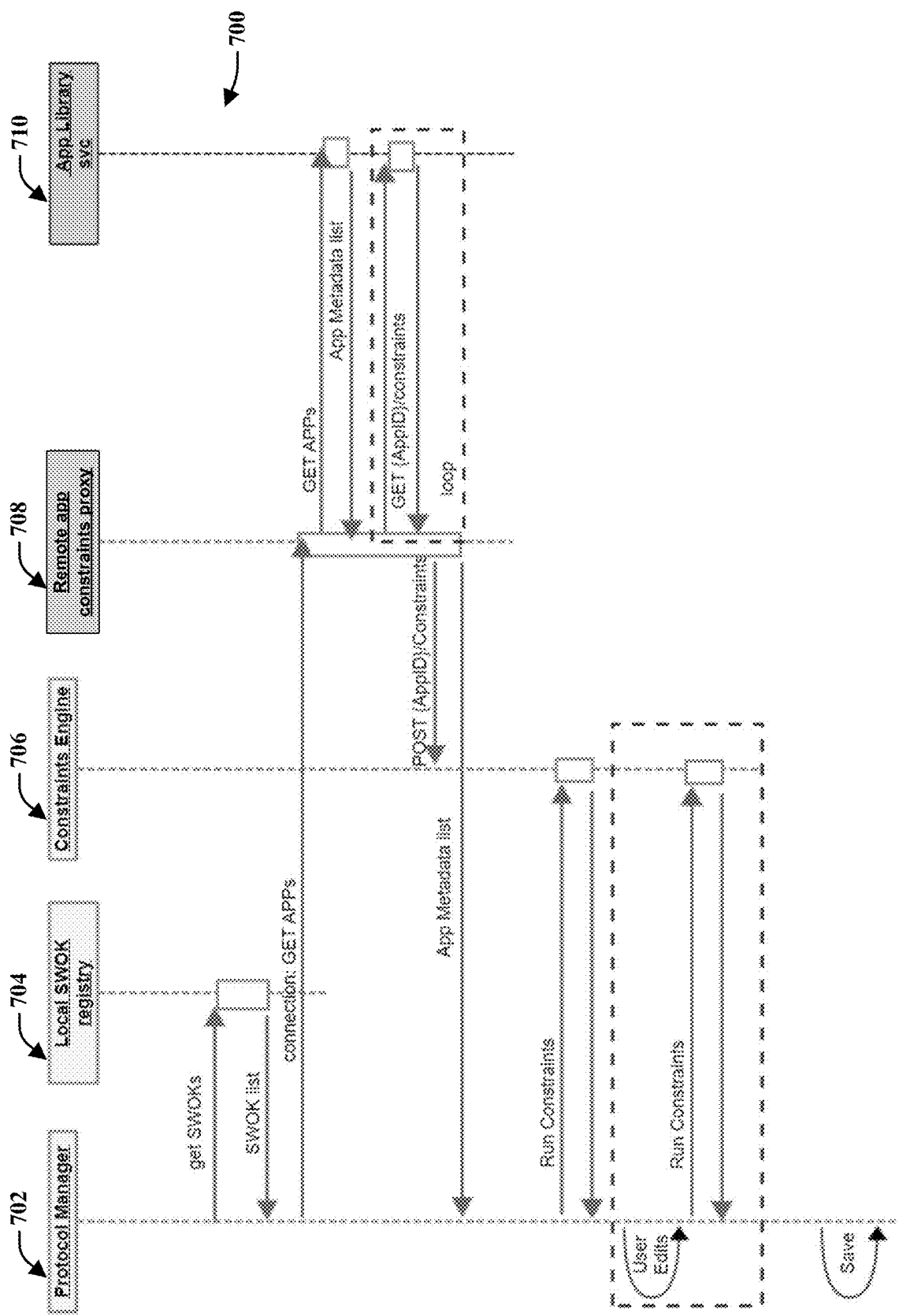
FIG. 7 is a block diagram of an exemplary sequence diagram in accordance with one or more embodiments described herein.

FIG. 7 illustrates a sequence diagram 700 in accordance with various embodiments described herein. A scanner can comprise a protocol manager 702, a local software option key (SWOK) registry 704, a constraints engine 706, and/or a remote application constraints proxy 708. It is noted that an edge system herein can comprise an applications library service 710. FIG. 7 can represent an order of operations starting from top to bottom, though this sequence is exemplary and other sequences and/or combinations can be implemented.

First, the protocol manager 702 can present (e.g., via a GUI) applications that are available. It is noted that a protocol herein can comprise a defined group of applications. Further, the protocol manager 702 can enable editing of a protocol herein. Available applications can be determined by retrieving software option keys (SWOKs) from the local SWOK registry 704 (e.g., catalog component 532), which can comprise application or software licenses and/or identify features or sections available to a medical scanner and/or a user. It is noted that the constrains engine can constrain features or options of a medical scanner (e.g., medical scanner 122). Additionally, applications can be accessed via the remote application constraints proxy 708 from the application library service 710. Further, associated metadata can be determined which can comprise associated constraints of respective applications (e.g., App IDs). App IDs and associated constraints can be returned to the constraints engine 706, and respective metadata can be returned to the protocol manager 702. Such metadata can be representative of how to present an application via a GUI herein, so that an associated protocol editing interface appears seamless and/or uniform. Such constraints can then be run. After each constraint edit, constraints can be checked to ensure that a user makes a valid selection. In this regard, constrains can be provided to the constraints engine 706.

Figure 8:
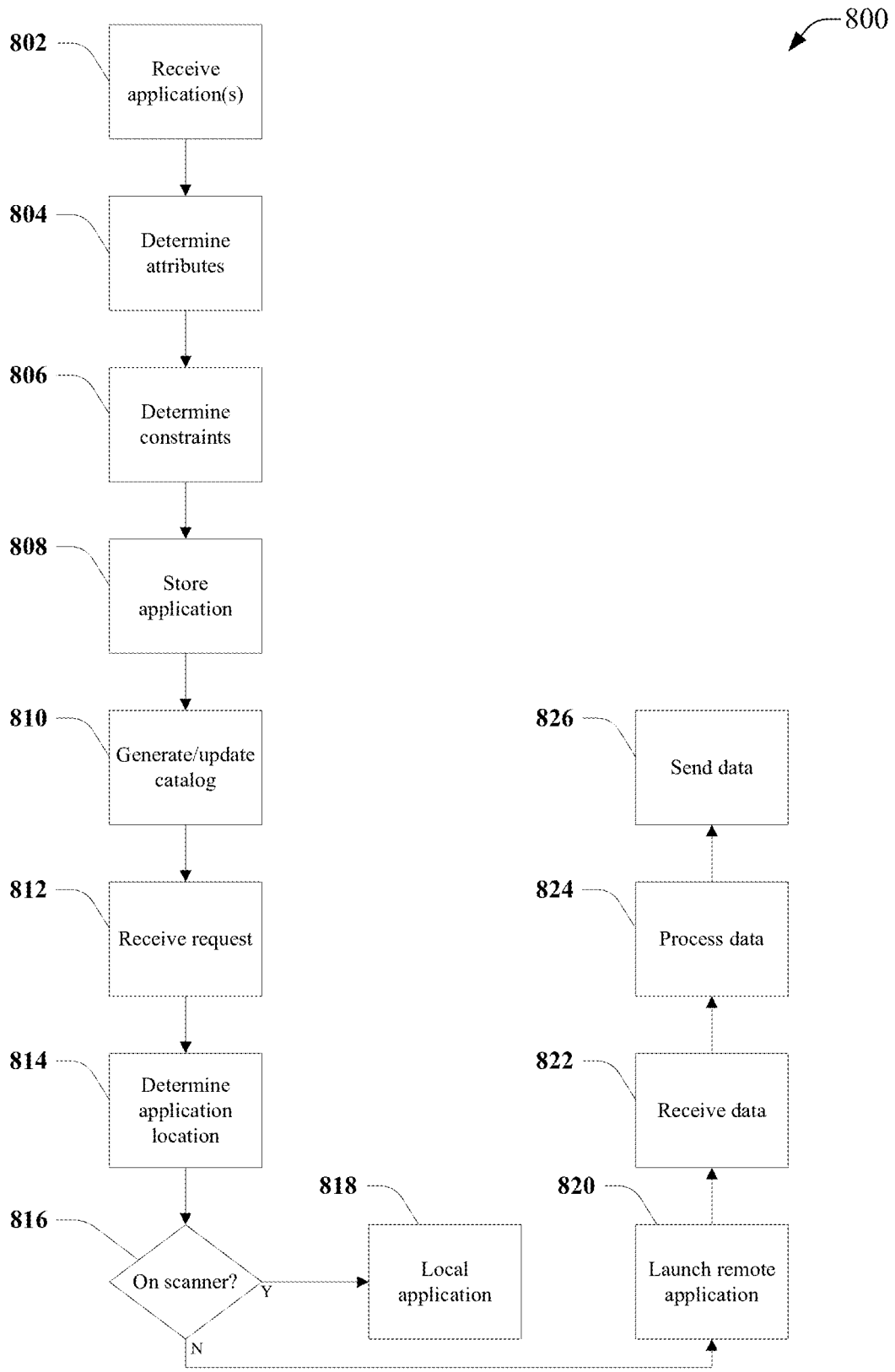
FIG. 8 is a flowchart for a process associated with medical scanners and associated components in accordance with one or more embodiments described herein.

Turning now to FIG. 8, there is illustrated a flowchart of a process 800 relating to medical scanners and associated components in accordance with one or more embodiments described herein. At 802 one or more applications can be received (e.g., via a communication component 112). For example, the one more applications can be received (e.g., via a network 120) from a device or another medical scanner. At 804, one or more attributes of the application can be determined (e.g., based on package schema data representative of a package schema of an application received (e.g., via a communication component 112) via a network (e.g., the network 120). At 806, based on one or more attributes of an application, constrains of the application applicable to a medical scanner can be determined (e.g., using a constraint component 118). At 808, the application can be stored (e.g., in an application database 116). At 810, a catalog of a catalog of applications executable via the medical scanner can be generated (e.g., using the catalog component 114). It is noted that the catalog of applications can comprise remote applications, and local applications stored in a memory of a medical scanner. At 812, a request to execute an application can be received (e.g., via a communication component 112) from an agent of a medical scanner. At 814, the location of the application can be determined (e.g., whether a local application or a remote application). If at 816, the application is a local application (e.g., stored on the medical scanner), the application can be locally executed via the medical scanner at 818 (e.g., using an agent component of the medical scanner). If at 816, the application is a remote application, the process can proceed to 820 at which the remote application is executed (e.g., using the execution component 204). At 822, data can be received from the medical scanner. In an embodiment, said data can comprise imaging data representative of a medical scan captured via the medical scanner. In this regard, executing an application at 820 can comprise processing the imaging data using the application. In other embodiments, the data can comprise patient workflow data or other suitable data. At 824 the data (e.g., the imaging data) can be processed (e.g., using the application executed using the execution component 204). At 822, in response to the processing the data (e.g., the imaging data), the data can be sent to the medical scanner or to a device communicatively coupled via a network (e.g., using the communication component 112).

Figure 9:
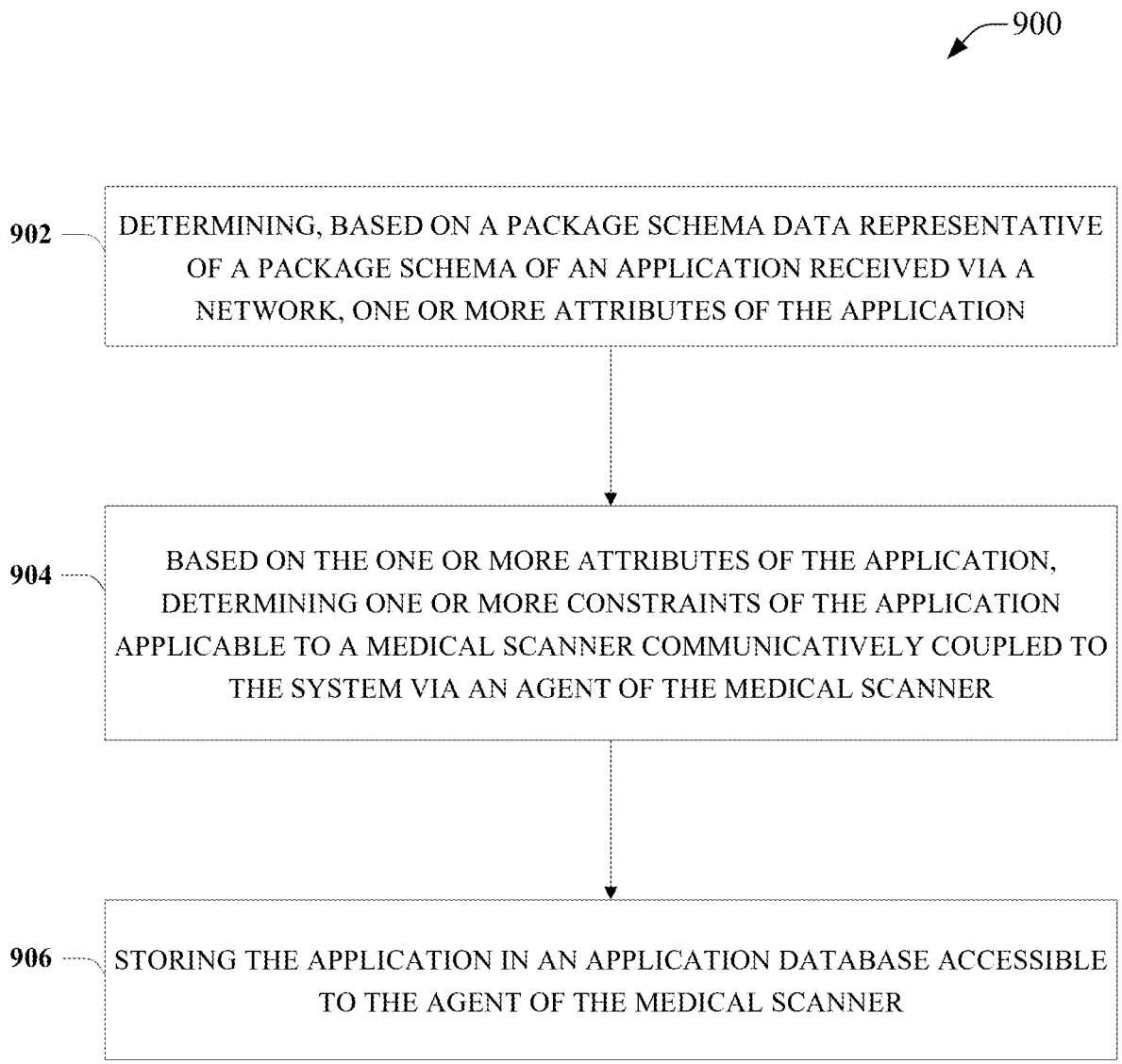
FIG. 9 is a block flow diagram for a process associated with medical scanners and associated components in accordance with one or more embodiments described herein.

FIG. 9 illustrates a block flow diagram for a process 900 associated with medical scanners and associated components in accordance with one or more embodiments described herein. At 902, the process 900 can comprise determining (e.g., using an attribute component 110), based on a package schema data representative of a package schema of an application received (e.g., using a communication component 112) via a network (e.g., network 120), one or more attributes of the application. At 904, the process 900 can comprise, based on the one or more attributes of the application, determining (e.g., using the constraint component 118) one or more constraints of the application applicable to a medical scanner (e.g., medical scanner 122) communicatively coupled to the system (e.g., system 102) via an agent (e.g., agent component 124) of the medical scanner. At 906, the process 900 can comprise storing (e.g., using the catalog component 114) the application in an application database (e.g., application database 116) accessible to the agent (e.g., agent component 124) of the medical scanner (e.g., medical scanner 122).

Figure 10:
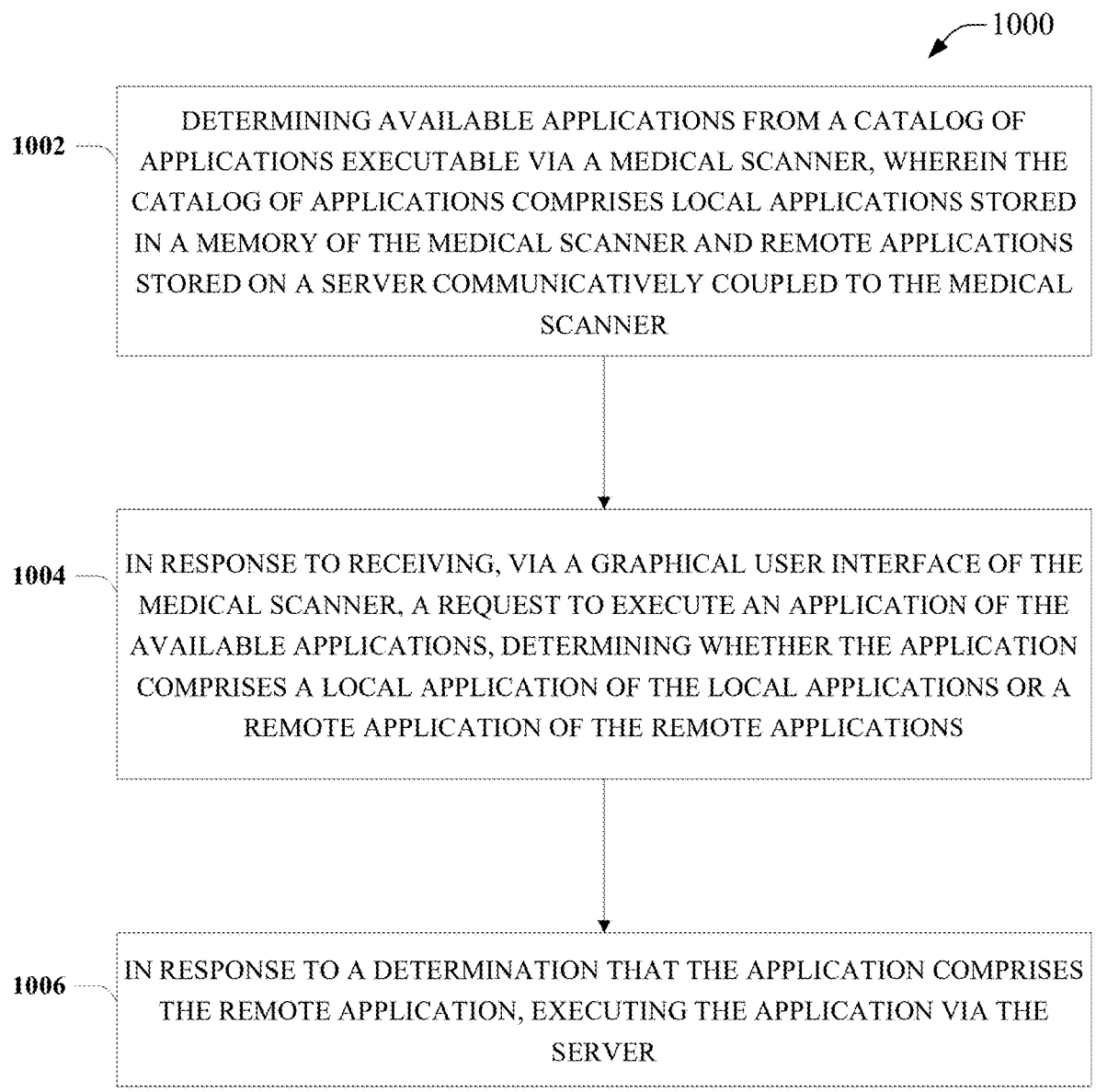
FIG. 10 is a block flow diagram for a process associated with medical scanners and associated components in accordance with one or more embodiments described herein.

FIG. 10 illustrates a block flow diagram for a process 1000 associated with medical scanners and associated components in accordance with one or more embodiments described herein. At 1002, the process 1000 can comprise determining (e.g., using an agent component 404) available applications from a catalog of applications executable via a medical scanner, wherein the catalog of applications comprises local applications stored in a memory (e.g., application storage 410) of the medical scanner and remote applications stored on a server (e.g., server 416) communicatively coupled (e.g., via the communication component 406) to the medical scanner. At 1004, the process 1000 can comprise, in response to receiving, via a graphical user interface of the medical scanner (e.g., GUI component 408), a request to execute an application of the available applications, determining (e.g., using the agent component 404) whether the application comprises a local application of the local applications or a remote application of the remote applications. At 1006, the process 1000 can comprise, in response to a determination (e.g., by the agent component 404) that the application comprises the remote application, executing (e.g., using the agent component 404) the application via the server (e.g., server 416).

Figure 11:
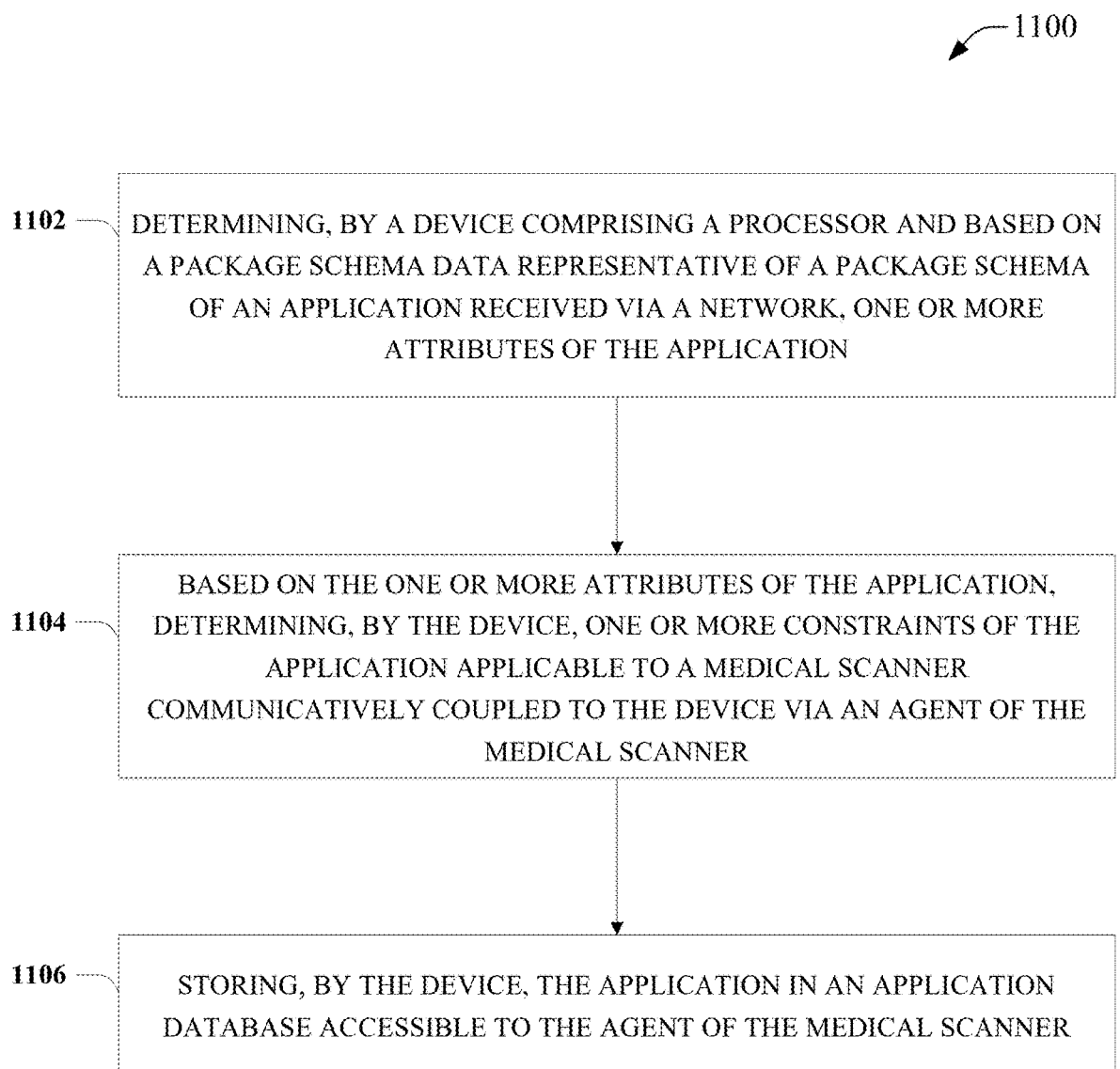
FIG. 11 is a block flow diagram for a process associated with medical scanners and associated components in accordance with one or more embodiments described herein.

FIG. 11 illustrates a block flow diagram for a process 1100 associated with medical scanners and associated components in accordance with one or more embodiments described herein. At 1102, the process 1100 can comprise determining, by a device comprising a processor (e.g., using an attribute component 110) and based on a package schema data representative of a package schema of an application received (e.g., using a communication component 112) via a network (e.g., network 120), one or more attributes of the application. At 1104, the process 1100 can comprise, based on the one or more attributes of the application, determining, by the device (e.g., using the constraint component 118), one or more constraints of the application applicable to a medical scanner (e.g., medical scanner 122) communicatively coupled to the device (e.g., system 102) via an agent (e.g., agent component 124) of the medical scanner. At 1106, the process 1100 can comprise storing, by the device (e.g., using the catalog component 114), the application in an application database (e.g., application database 116) accessible to the agent of the medical scanner (e.g., medical scanner 122).

Figure 12:
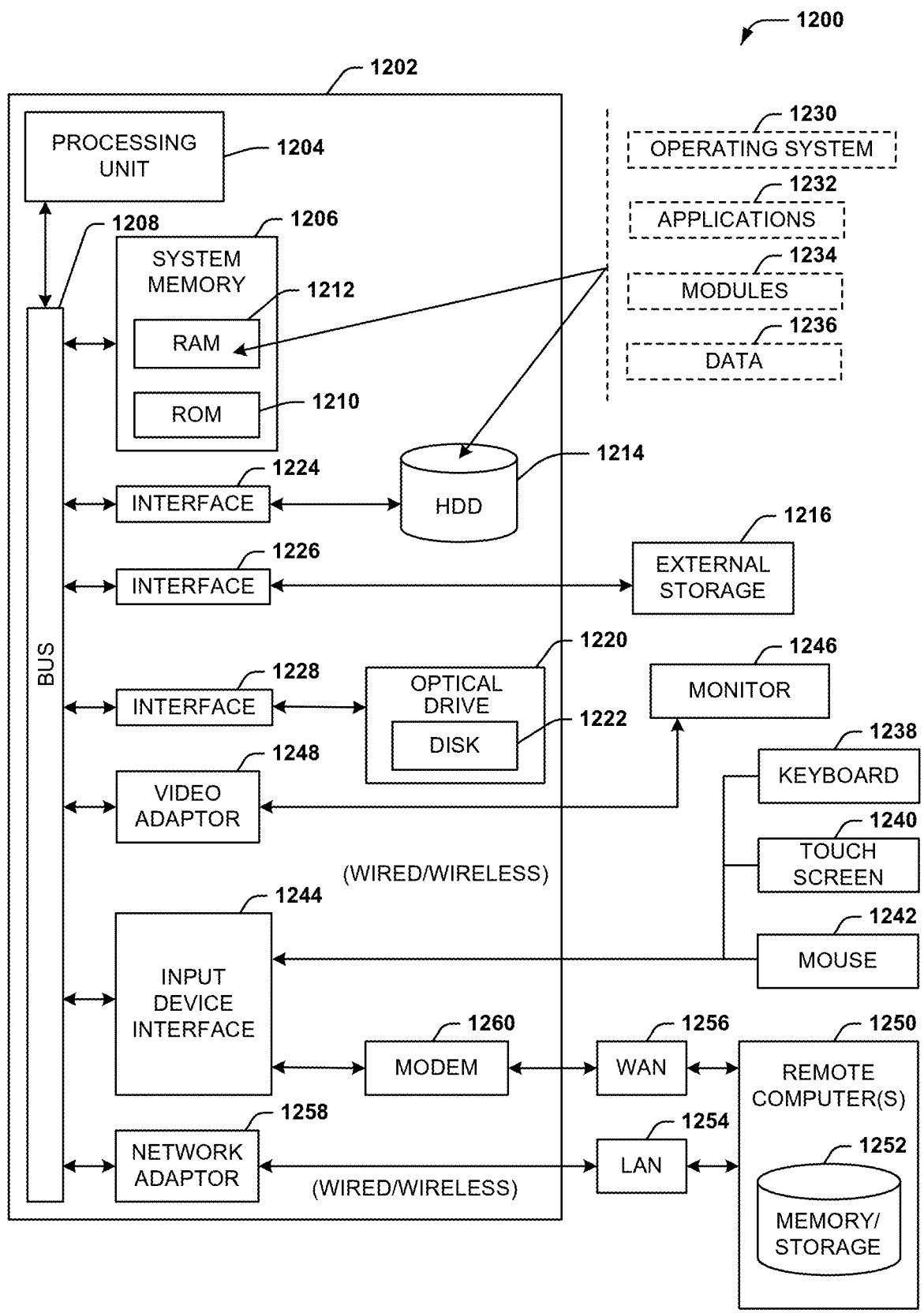
FIG. 12 is an example, non-limiting computing environment in which one or more embodiments described herein can be implemented.

In order to provide additional context for various embodiments described herein, FIG. 12 and the following discussion are intended to provide a brief, general description of a suitable computing environment 1200 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the various methods can be practiced with other computer system configurations, including single-processor or multiprocessor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data, or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory, or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries, or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared, and other wireless media.

With reference again to FIG. 12, the example environment 1200 for implementing various embodiments of the aspects described herein includes a computer 1202, the computer 1202 including a processing unit 1204, a system memory 1206 and a system bus 1208. The system bus 1208 couples system components including, but not limited to, the system memory 1206 to the processing unit 1204. The processing unit 1204 can be any of various commercially available processors. Dual microprocessors and other multi-processor architectures can also be employed as the processing unit 1204.

The system bus 1208 can be any of several types of bus structure that can further interconnect to a memory bus (with or without a memory controller), a peripheral bus, and a local bus using any of a variety of commercially available bus architectures. The system memory 1206 includes ROM 1210 and RAM 1212. A basic input/output system (BIOS) can be stored in a non-volatile memory such as ROM, erasable programmable read only memory (EPROM), EEPROM, which BIOS contains the basic routines that help to transfer information between elements within the computer 1202, such as during startup. The RAM 1212 can also include a high-speed RAM such as static RAM for caching data.

The computer 1202 further includes an internal hard disk drive (HDD) 1214 (e.g., EIDE, SATA), one or more external storage devices 1216 (e.g., a magnetic floppy disk drive (FDD) 1216, a memory stick or flash drive reader, a memory card reader, etc.) and an optical disk drive 1220 (e.g., which can read or write from a CD-ROM disc, a DVD, a BD, etc.). While the internal HDD 1214 is illustrated as located within the computer 1202, the internal HDD 1214 can also be configured for external use in a suitable chassis (not shown). Additionally, while not shown in environment 1200, a solid-state drive (SSD) could be used in addition to, or in place of, an HDD 1214. The HDD 1214, external storage device(s) 1216 and optical disk drive 1220 can be connected to the system bus 1208 by an HDD interface 1224, an external storage interface 1226 and an optical drive interface 1228, respectively. The interface 1224 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 1202, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 1212, including an operating system 1230, one or more application programs 1232, other program modules 1234 and program data 1236. All or portions of the operating system, applications, modules, and/or data can also be cached in the RAM 1212. The systems and methods described herein can be implemented utilizing various commercially available operating systems or combinations of operating systems.

Computer 1202 can optionally comprise emulation technologies. For example, a hypervisor (not shown) or other intermediary can emulate a hardware environment for operating system 1230, and the emulated hardware can optionally be different from the hardware illustrated in FIG. 12. In such an embodiment, operating system 1230 can comprise one virtual machine (VM) of multiple VMs hosted at computer 1202. Furthermore, operating system 1230 can provide runtime environments, such as the Java runtime environment or the .NET framework, for applications 1232. Runtime environments are consistent execution environments that allow applications 1232 to run on any operating system that includes the runtime environment. Similarly, operating system 1230 can support containers, and applications 1232 can be in the form of containers, which are lightweight, standalone, executable packages of software that include, e.g., code, runtime, system tools, system libraries and settings for an application.

Further, computer 1202 can be enable with a security module, such as a trusted processing module (TPM). For instance, with a TPM, boot components hash next in time boot components, and wait for a match of results to secured values, before loading a next boot component. This process can take place at any layer in the code execution stack of computer 1202, e.g., applied at the application execution level or at the operating system (OS) kernel level, thereby enabling security at any level of code execution.

A user can enter commands and information into the computer 1202 through one or more wired/wireless input devices, e.g., a keyboard 1238, a touch screen 1240, and a pointing device, such as a mouse 1242. Other input devices (not shown) can include a microphone, an infrared (IR) remote control, a radio frequency (RF) remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 1204 through an input device interface 1244 that can be coupled to the system bus 1208, but can be connected by other interfaces, such as a parallel port, an IEEE 1394 serial port, a game port, a USB port, an IR interface, a BLUETOOTH® interface, etc.

A monitor 1246 or other type of display device can be also connected to the system bus 1208 via an interface, such as a video adapter 1248. In addition to the monitor 1246, a computer typically includes other peripheral output devices (not shown), such as speakers, printers, etc.

The computer 1202 can operate in a networked environment using logical connections via wired and/or wireless communications to one or more remote computers, such as a remote computer(s) 1250. The remote computer(s) 1250 can be a workstation, a server computer, a router, a personal computer, portable computer, microprocessor-based entertainment appliance, a peer device or other common network node, and typically includes many or all of the elements described relative to the computer 1202, although, for purposes of brevity, only a memory/storage device 1252 is illustrated. The logical connections depicted include wired/wireless connectivity to a local area network (LAN) 1254 and/or larger networks, e.g., a wide area network (WAN) 1256. Such LAN and WAN networking environments are commonplace in offices and companies, and facilitate enterprise-wide computer networks, such as intranets, all of which can connect to a global communications network, e.g., the Internet.

When used in a LAN networking environment, the computer 1202 can be connected to the local network 1254 through a wired and/or wireless communication network interface or adapter 1258. The adapter 1258 can facilitate wired or wireless communication to the LAN 1254, which can also include a wireless access point (AP) disposed thereon for communicating with the adapter 1258 in a wireless mode.

When used in a WAN networking environment, the computer 1202 can include a modem 1260 or can be connected to a communications server on the WAN 1256 via other means for establishing communications over the WAN 1256, such as by way of the Internet. The modem 1260, which can be internal or external and a wired or wireless device, can be connected to the system bus 1208 via the input device interface 1244. In a networked environment, program modules depicted relative to the computer 1202 or portions thereof, can be stored in the remote memory/storage device 1252. It will be appreciated that the network connections shown are example and other means of establishing a communications link between the computers can be used.

When used in either a LAN or WAN networking environment, the computer 1202 can access cloud storage systems or other network-based storage systems in addition to, or in place of, external storage devices 1216 as described above. Generally, a connection between the computer 1202 and a cloud storage system can be established over a LAN 1254 or WAN 1256 e.g., by the adapter 1258 or modem 1260, respectively. Upon connecting the computer 1202 to an associated cloud storage system, the external storage interface 1226 can, with the aid of the adapter 1258 and/or modem 1260, manage storage provided by the cloud storage system as it would other types of external storage. For instance, the external storage interface 1226 can be configured to provide access to cloud storage sources as if those sources were physically connected to the computer 1202.

The computer 1202 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

Figure 13:
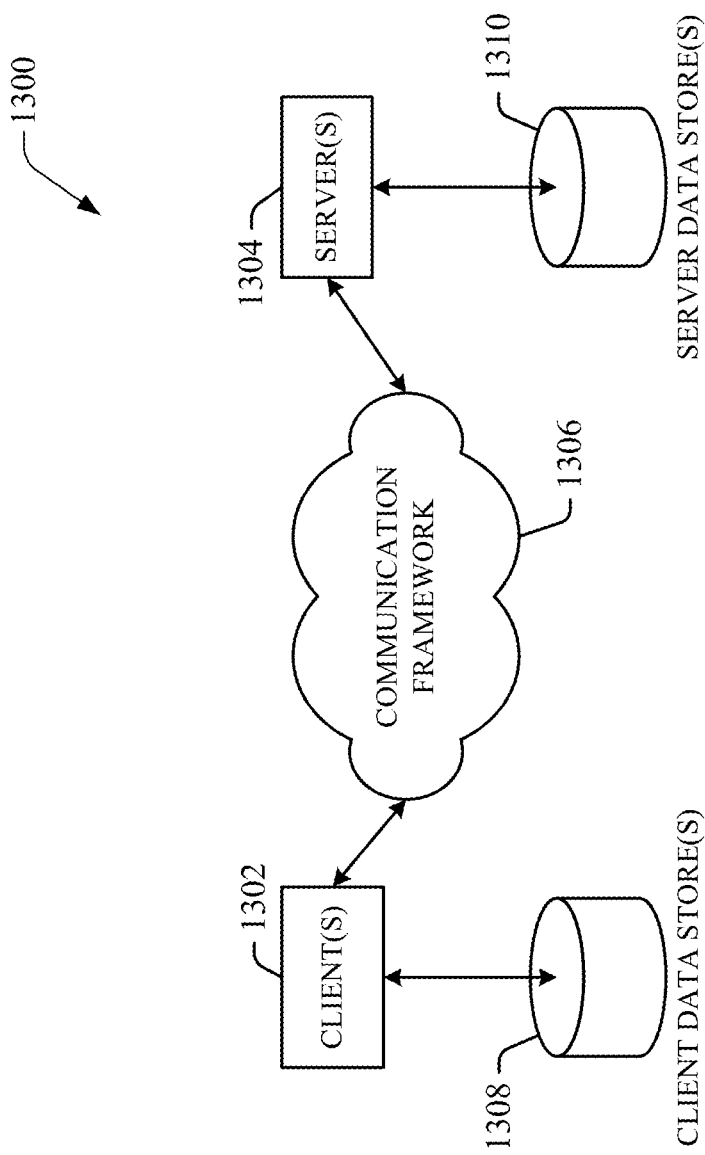
FIG. 13 is an example, non-limiting networking environment in which one or more embodiments described herein can be implemented.

Referring now to FIG. 13, there is illustrated a schematic block diagram of a computing environment 1300 in accordance with this specification. The system 1300 includes one or more client(s) 1302, (e.g., computers, smart phones, tablets, cameras, PDA's). The client(s) 1302 can be hardware and/or software (e.g., threads, processes, computing devices). The client(s) 1302 can house cookie(s) and/or associated contextual information by employing the specification, for example.

The system 1300 also includes one or more server(s) 1304. The server(s) 1304 can also be hardware or hardware in combination with software (e.g., threads, processes, computing devices). The servers 1304 can house threads to perform transformations of media items by employing aspects of this disclosure, for example. One possible communication between a client 1302 and a server 1304 can be in the form of a data packet adapted to be transmitted between two or more computer processes wherein data packets may include coded analyzed headspaces and/or input. The data packet can include a cookie and/or associated contextual information, for example. The system 1300 includes a communication framework 1306 (e.g., a global communication network such as the Internet) that can be employed to facilitate communications between the client(s) 1302 and the server(s) 1304.

Communications can be facilitated via a wired (including optical fiber) and/or wireless technology. The client(s) 1302 are operatively connected to one or more client data store(s) 1308 that can be employed to store information local to the client(s) 1302 (e.g., cookie(s) and/or associated contextual information). Similarly, the server(s) 1304 are operatively connected to one or more server data store(s) 1310 that can be employed to store information local to the servers 1304.

In one exemplary implementation, a client 1302 can transfer an encoded file, (e.g., encoded media item), to server 1304. Server 1304 can store the file, decode the file, or transmit the file to another client 1302. It is noted that a client 1302 can also transfer uncompressed file to a server 1304 and server 1304 can compress the file and/or transform the file in accordance with this disclosure. Likewise, server 1304 can encode information and transmit the information via communication framework 1306 to one or more clients 1302.

The illustrated aspects of the disclosure may also be practiced in distributed computing environments where certain tasks are performed by remote processing devices that are linked through a communications network. In a distributed computing environment, program modules can be located in both local and remote memory storage devices.

The above description includes non-limiting examples of the various embodiments. It is, of course, not possible to describe every conceivable combination of components or methods for purposes of describing the disclosed subject matter, and one skilled in the art may recognize that further combinations and permutations of the various embodiments are possible. The disclosed subject matter is intended to embrace all such alterations, modifications, and variations that fall within the spirit and scope of the appended claims.

With regard to the various functions performed by the above-described components, devices, circuits, systems, etc., the terms (including a reference to a "means") used to describe such components are intended to also include, unless otherwise indicated, any structure(s) which performs the specified function of the described component (e.g., a functional equivalent), even if not structurally equivalent to the disclosed structure. In addition, while a particular feature of the disclosed subject matter may have been disclosed with respect to only one of several implementations, such feature may be combined with one or more other features of the other implementations as may be desired and advantageous for any given or particular application.

The terms "exemplary" and/or "demonstrative" as used herein are intended to mean serving as an example, instance, or illustration. For the avoidance of doubt, the subject matter disclosed herein is not limited by such examples. In addition, any aspect or design described herein as "exemplary" and/or "demonstrative" is not necessarily to be construed as preferred or advantageous over other aspects or designs, nor is it meant to preclude equivalent structures and techniques known to one skilled in the art. Furthermore, to the extent that the terms "includes," "has," "contains," and other similar words are used in either the detailed description or the claims, such terms are intended to be inclusive—in a manner similar to the term "comprising" as an open transition word—without precluding any additional or other elements.

The term "or" as used herein is intended to mean an inclusive "or" rather than an exclusive "or." For example, the phrase "A or B" is intended to include instances of A, B, and both A and B. Additionally, the articles "a" and "an" as used in this application and the appended claims should generally be construed to mean "one or more" unless either otherwise specified or clear from the context to be directed to a singular form.

The term "set" as employed herein excludes the empty set, i.e., the set with no elements therein. Thus, a "set" in the subject disclosure includes one or more elements or entities. Likewise, the term "group" as utilized herein refers to a collection of one or more entities.

The description of illustrated embodiments of the subject disclosure as provided herein, including what is described in the Abstract, is not intended to be exhaustive or to limit the disclosed embodiments to the precise forms disclosed. While specific embodiments and examples are described herein for illustrative purposes, various modifications are possible that are considered within the scope of such embodiments and examples, as one skilled in the art can recognize. In this regard, while the subject matter has been described herein in connection with various embodiments and corresponding drawings, where applicable, it is to be understood that other similar embodiments can be used or modifications and additions can be made to the described embodiments for performing the same, similar, alternative, or substitute function of the disclosed subject matter without deviating therefrom. Therefore, the disclosed subject matter should not be limited to any single embodiment described herein, but rather should be construed in breadth and scope in accordance with the appended claims below.

What is claimed is:

1. A system, comprising:
   a memory that stores computer executable components; and
   a processor that executes at least one of the computer executable components that:
   determines one or more first attributes of an application based on package schema data representative of a package schema of the application received via a network;
   determines one or more second attributes of a medical scanner device communicatively coupled to the system;
   based on a comparison of the one or more first attributes of the application and the one or more second attributes of the medical scanner device, determines one or more constraints of the application applicable to the medical scanner device;
   stores, in an application database accessible to the medical scanner device, the application and the one or more constraints of the application applicable to the medical scanner device, wherein portions of a user interface associated with the medical scanner device that are related to one or more portions of the application are restricted based on the one or more constraints, wherein the application and the one or more constraints are accessible via the user interface associated with the medical scanner device;
   receives, from the medical scanner device, a request to execute the application; and
   in response to receiving the request from the medical scanner device to execute the application, executes the application according to the one or more constraints of the application applicable to the medical scanner device.

2. The system of claim 1, wherein the at least one of the computer executable components further:
   receives imaging data representative of a medical scan captured via the medical scanner device; and
   executes the application to process the imaging data.

3. The system of claim 2, wherein the at least one of the computer executable components further:
   sends the processed imaging data to the medical scanner device in response to the imaging data being processed using the application executing remotely from the medical scanner device.

4. The system of claim 2, wherein the at least one of the computer executable components further:
   sends the processed imaging data to a device communicatively coupled to the system via the network in response to the imaging data being processed using the application.

5. The system of claim 1, wherein the application comprises a remote application of a group of remote applications stored in the application database and not installed on the medical scanner device, and wherein the at least one of the computer executable components further:
   generates a catalog of applications executable on data produced by the medical scanner device, and wherein the catalog of applications comprises the group of remote applications and local applications stored in a memory of the medical scanner device.

6. The system of claim 5, wherein the request to execute the application is received in response to a determination that the application comprises the remote application.

7. The system of claim 1, wherein the at least one of the computer executable components further:
determines the package schema based on machine learning applied to past package schemas of past applications other than the application.

8. The system of claim 1, wherein the at least one of the computer executable components further:
determines the one or more constraints based further on machine learning applied to past constraints of past applications other than the application.

9. The system of claim 1, wherein the application comprises a patient setup workflow application.

10. The system of claim 1, wherein the application comprises a remote reconstruction application.

11. The system of claim 1, wherein the application comprises a post-processing application.

12. A method, comprising:
determining, by a system comprising a processor and based on package schema data representative of a package schema of an application received via a network, one or more first attributes of the application;
determining, by the system, one or more second attributes of a medical scanner device communicatively coupled to the system;
based on a comparison of the one or more first attributes of the application and the one or more second attributes of the medical scanner device, determining, by the system, one or more constraints of the application applicable to the medical scanner device;
storing, by the system, the application and the one or more constraints of the application applicable to the medical scanner device in an application database accessible to the medical scanner device, wherein portions of a user interface associated with the medical scanner device that are related to one or more portions of the application are restricted based on the one or more constraints, wherein the application and the one or more constraints are accessible via the user interface associated with the medical scanner device;
receiving, by the system, from the medical scanner device, a request to execute the application; and
in response to receiving the request from the medical scanner device to execute the application, executes, by the system, the application according to the one or more constraints of the application applicable to the medical scanner device.

13. The method of claim 12, wherein the one or more constraints are associated with one or more features of the medical scanner device.

14. The method of claim 12, wherein the medical scanner device comprises a computed tomography scanner, a positron emission tomography scanner, magnetic resonance imaging scanner, or an ultrasound scanner.

15. The method of claim 12, wherein the medical scanner device is located in a first location comprising a medical facility, and wherein the system is located in a second location, different from the first location.

16. The method of claim 12, further comprising:
receiving, by the system, imaging data representative of a medical scan captured via the medical scanner device; and
executing, by the system, the application to process the imaging data.

17. A non-transitory machine-readable medium, comprising executable instructions that, when executed by a processor of a system, facilitate performance of operations, comprising:
determining, based on package schema data representative of a package schema of an application received via a network, one or more first attributes of the application;
determining one or more second attributes of a medical scanner device communicatively coupled to the system;
determining, based on a comparison of the one or more first attributes of the application and the one or more second attributes of the medical scanner device, one or more constraints of the application applicable to the medical scanner device;
storing the application and the one or more constraints of the application applicable to the medical scanner device in an application database accessible to the medical scanner device, wherein portions of a user interface associated with the medical scanner device that are related to one or more portions of the application are restricted based on the one or more constraints, wherein the application and the one or more constraints are accessible via the user interface associated with the medical scanner device;
receiving, from the medical scanner device, a request to execute the application; and
in response to receiving the request from the medical scanner device to execute the application, executing the application according to the one or more constraints of the application applicable to the medical scanner device.

18. The non-transitory machine-readable medium of claim 17, wherein the one or more constraints are associated with one or more features of the medical scanner device.

19. The non-transitory machine-readable medium of claim 17, wherein the medical scanner device comprises a computed tomography scanner, a positron emission tomography scanner, magnetic resonance imaging scanner, or an ultrasound scanner.

20. The non-transitory machine-readable medium of claim 17, wherein the medical scanner device is located in a first location comprising a medical facility, and wherein the system is located in a second location, different from the first location.

* * * * *